(12) United States Patent
Meskens et al.

(10) Patent No.: US 10,425,751 B2
(45) Date of Patent: Sep. 24, 2019

(54) DUAL POWER SUPPLY

(71) Applicant: Cochlear Limited, Macquarie University (AU)

(72) Inventors: Werner Meskens, Opwijk (BE); Tony Nygard, Terrigal (AU); Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 122 days.

(21) Appl. No.: 15/165,443

(22) Filed: May 26, 2016

(65) Prior Publication Data

US 2017/0180887 A1    Jun. 22, 2017

Related U.S. Application Data

(60) Provisional application No. 62/269,507, filed on Dec. 18, 2015.

(51) Int. Cl.
| | |
|---|---|
| *A61N 1/378* | (2006.01) |
| *H04R 25/00* | (2006.01) |
| *H02J 7/00* | (2006.01) |
| *H02M 7/08* | (2006.01) |
| *H02J 7/02* | (2016.01) |

(Continued)

(52) U.S. Cl.
CPC ......... *H04R 25/602* (2013.01); *A61N 1/3787* (2013.01); *H02J 7/0044* (2013.01); *H02J 7/0068* (2013.01); *H02J 7/025* (2013.01); *H02J 50/12* (2016.02); *H02M 7/08* (2013.01); *H04B 5/0031* (2013.01); *H04B 5/0037* (2013.01); *H04B 5/0081* (2013.01); *H04R 25/305* (2013.01); *H04R 25/554* (2013.01);

(Continued)

(58) Field of Classification Search
CPC .............. A61N 1/0541; A61N 1/36036; A61N 1/36038; A61N 1/372; A61N 1/37211; A61N 1/37223; A61N 1/378; A61N 1/3787

See application file for complete search history.

(56) References Cited

U.S. PATENT DOCUMENTS

| | | | |
|---|---|---|---|
| 6,219,580 B1 | 4/2001 | Faltys et al. | |
| 6,542,777 B1 | 4/2003 | Griffith et al. | |
| (Continued) | | | |

FOREIGN PATENT DOCUMENTS

| | | |
|---|---|---|
| WO | 2006112410 A1 | 10/2006 |
| WO | WO2008101151 A2 | 8/2008 |
| WO | 2014178345 A1 | 11/2014 |

OTHER PUBLICATIONS

PCT International Search Report; International application No. PCT/IB2016/057747, dated Mar. 16, 2017, 4 pages.

(Continued)

*Primary Examiner* — Allen Porter
(74) *Attorney, Agent, or Firm* — Edell, Shapiro & Finnan, LLC

(57) ABSTRACT

A device comprises a tank circuit including a parallel tank circuit and a series tank circuit. In this example, the parallel tank circuit and the series tank circuit share a capacitive component and an inductive component. The device also includes electronics, and circuitry configured to selectively couple the electronics to the parallel tank circuit for a first application and to couple the electronics to the series tank circuit for a second application.

23 Claims, 10 Drawing Sheets

(51) Int. Cl.
*H04B 5/00* (2006.01)
*H02J 50/12* (2016.01)

(52) U.S. Cl.
CPC ........ *H04R 25/606* (2013.01); *H04R 2225/31* (2013.01); *H04R 2225/33* (2013.01)

(56) References Cited

U.S. PATENT DOCUMENTS

| | | | |
|---|---|---|---|
| 7,720,546 B2 | 5/2010 | Ginggen et al. | |
| 2002/0183801 A1 | 12/2002 | Howard et al. | |
| 2004/0260361 A1* | 12/2004 | Gibson | A61N 1/0541 607/57 |
| 2005/0085873 A1* | 4/2005 | Gord | A61N 1/372 607/61 |
| 2009/0281597 A1 | 11/2009 | Parramon et al. | |
| 2010/0106223 A1* | 4/2010 | Grevious | A61N 1/3706 607/60 |
| 2010/0114215 A1 | 5/2010 | Burnes et al. | |
| 2011/0101790 A1* | 5/2011 | Budgett | H02J 50/12 307/104 |
| 2014/0025137 A1 | 1/2014 | Meskens | |
| 2014/0249603 A1 | 9/2014 | Yan et al. | |
| 2014/0270296 A1 | 9/2014 | Fort et al. | |
| 2016/0049800 A1 | 2/2016 | Tanaka et al. | |

OTHER PUBLICATIONS

PCT Written Opinion of the International Searching Authority, PCT/IB2016/057747, dated Mar. 16, 2017, 8 pages.

Design of Inductive Wireless Power Systems for Consumer Electronics, WIPOS, Apr. 2013-Sep. 2014, pp. 1-65.

Extended European Search Report in corresponding European Application No. 16875040.4, dated Jun. 3, 2019, 10 pages.

\* cited by examiner

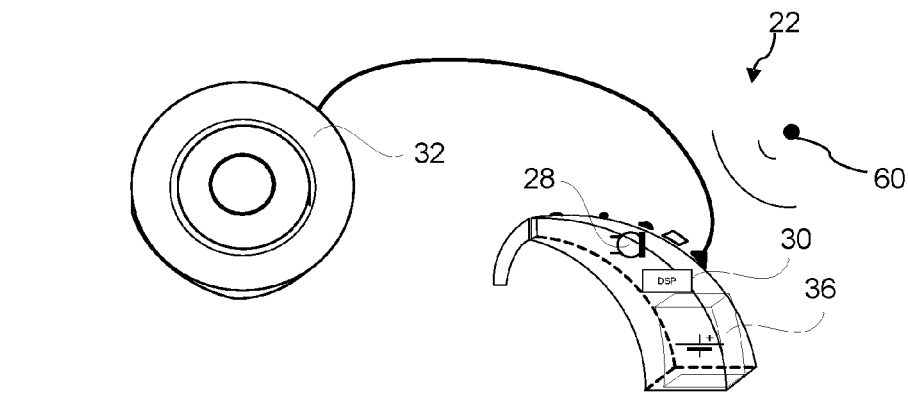
FIG. 4
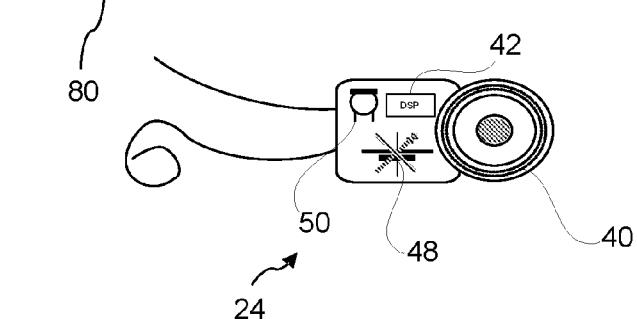
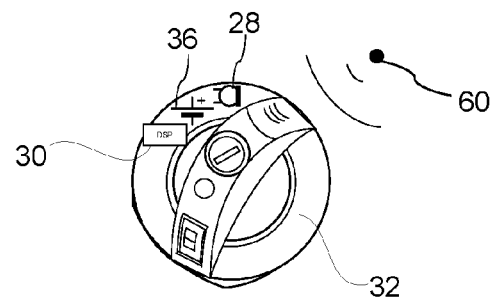
FIG. 5
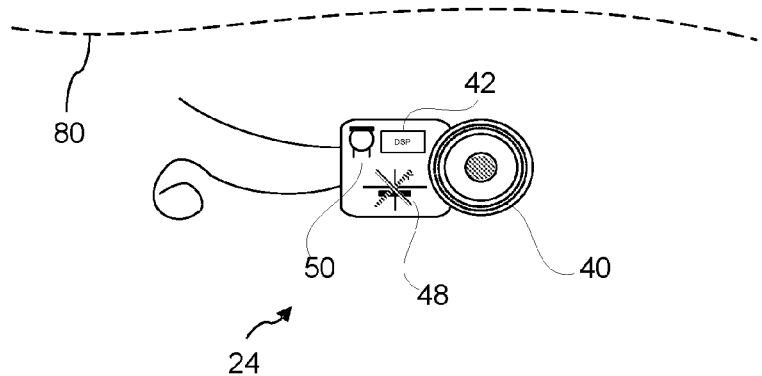

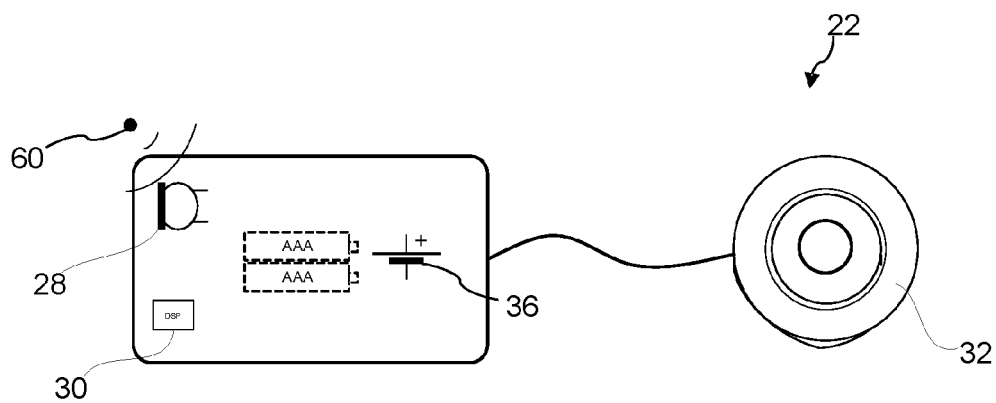
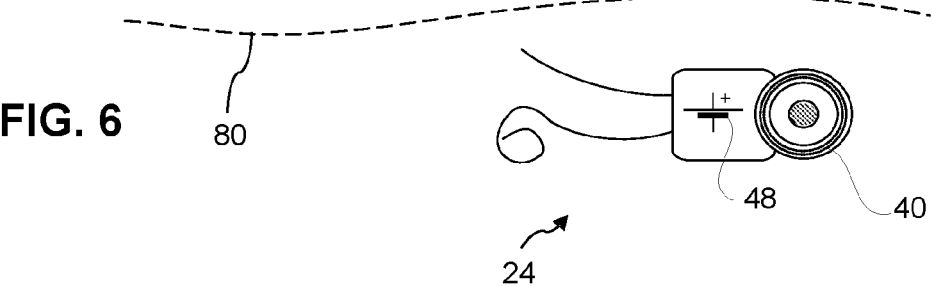
FIG. 6
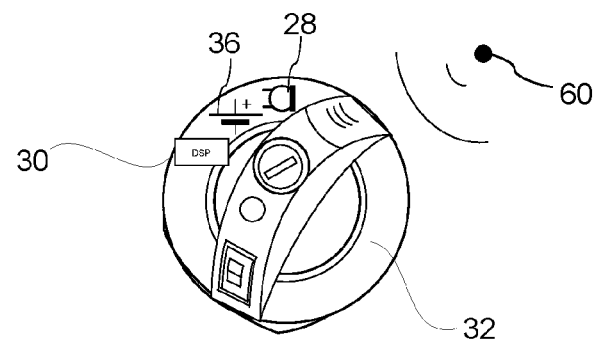
FIG. 7
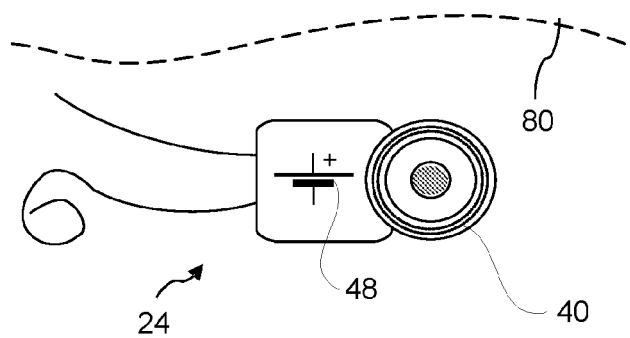

DUAL POWER SUPPLY

CROSS-REFERENCE TO RELATED APPLICATION

This application claims priority to U.S. Provisional Patent Application No. 62/269,507 filed on Dec. 18, 2015, the entirety of which is incorporated herein by reference.

BACKGROUND

Various types of hearing prostheses provide persons with different types of hearing loss with the ability to perceive sound. Generally, hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Example hearing prostheses include traditional hearing aids, vibration-based hearing devices, cochlear implants, and auditory brainstem implants. A traditional hearing aid, which is an acoustic stimulation device, typically includes a small microphone to detect sound, an amplifier to amplify certain portions of the detected sound, and a speaker to transmit the amplified sounds into the person's ear canal.

A vibration-based hearing device, which is also an acoustic stimulation device, typically includes a microphone to detect sound and a vibration mechanism to apply mechanical vibrations corresponding to the detected sound directly to a person, thereby causing vibrations in the person's inner ear. Vibration-based hearing devices include, for example, bone conduction devices, middle ear devices, and direct acoustic cochlear stimulation devices. A bone conduction device transmits vibrations corresponding to sound via the teeth and/or skull. A so-called middle ear device transmits vibrations corresponding to sound via the middle ear (i.e., the ossicular chain), without using the teeth or skull. A direct acoustic cochlear stimulation device transmits vibrations corresponding to sound via the inner ear (i.e., the cochlea), without using the teeth, skull or middle ear.

A cochlear implant provides a person with the ability to perceive sound by stimulating the person's auditory nerve via an array of electrodes implanted in the person's cochlea. A microphone coupled to the cochlear implant detects sound waves, which are converted into a series of electrical stimulation signals that are delivered to the implant recipient's cochlea via the array of electrodes. An auditory brainstem implant may use technology similar to a cochlear implant, but instead of applying electrical stimulation to a person's cochlea, the auditory brainstem implant applies electrical stimulation directly to a person's brain stem, bypassing the cochlea altogether. Electrically stimulating auditory nerves in a cochlea with a cochlear implant or electrically stimulating a brainstem may enable persons with hearing loss to perceive sound.

Further, some persons may benefit from a hearing prosthesis that combines two or more characteristics of the traditional hearing aids, vibration-based hearing devices, cochlear implants, or auditory brainstem implants (e.g., two or more modes of stimulation) to enable the person to perceive sound. Such hearing prostheses can be referred to as bimodal hearing prostheses. Still other persons benefit from two hearing prostheses, one for each ear (e.g., a so-called binaural system generally or a bilateral system for persons with two cochlear implants).

SUMMARY

Some hearing prostheses include separate units or elements that function together to enable the person to perceive sound. In one example, a hearing prosthesis includes a first element that is external to the person and a second element that may be implanted in the person. In the present example, the first element is configured to detect sound, to encode the detected sound as acoustic signals, to deliver the acoustic signals to the second element over a coupling or link between the first and second elements, and to deliver power to the second element over the link. The second element is configured to apply the delivered acoustic signals as output signals to the person's hearing system, and to apply the delivered power to one or more components of the second element. The output signals applied to the person's hearing system can include, for example, audible signals, vibrations, and electrical signals, as described generally above. In one example, the second element is also configured to detect sound, to encode the detected sound as acoustic signals, as well as to apply the acoustic signals as output signals to the person's hearing system.

The coupling or link between the first and second elements can be a radio frequency (RF) link operating in the magnetic or electric near-field, for example, and can be utilized to operate the hearing prosthesis in one or more modes, such as applying output signals to the person's hearing system and charging a battery of the hearing prosthesis. The present disclosure is directed to devices, systems, and methods for controlling a data and/or power coupling for different load or power conditions of a device or system. In one example, the coupling is configured to transfer electrical signals to deliver power and encoded data together. In another example, the coupling is configured to transfer electrical signals to deliver power without encoded data. Further, in various non-limiting examples, the system is directed to a hearing prosthesis, such as a cochlear implant, a bone anchored device, a direct acoustic cochlear stimulation device, an auditory brain stem implant, or any other type of hearing prosthesis configured to assist a recipient in perceiving sound.

More particularly, in one example, an RF front-end of the second element integrates a dual power supply mode using a relatively low component count. In this example, the RF front-end includes a dual power supply configuration that includes first and second rectifier circuits. The first rectifier circuit is coupled to a receiving coil over a parallel resonant tank and the second rectifier circuit is coupled to the receiving coil over a series resonant tank. In this example, the parallel resonant tank and the series resonant tank make use of the same inductive and capacitive components, e.g., the same LC circuit.

A first type of power supply of the dual power supply configuration uses the parallel resonant tank and is intended to provide power (e.g., less than 10 mW) for lower loads (higher Rload). The first type of power supply is a voltage controlled power supply. One use of such a power supply is to provide power to electrical components, circuits, and/or stimulation electrodes when there is no separate battery (or other power source) coupled directly to such components.

A second type of power supply of the dual power supplies uses the series resonant tank and is intended to provide power (e.g., greater than 10 mW) for higher loads (lower Rload). The second type of power supply is a current controlled power supply. One use of such a power supply is to recharge a battery coupled to electrical components, circuits, and/or stimulation electrodes.

Various aspects and examples are described herein as being implemented by methods and/or systems (such as, a hearing prosthesis system).

BRIEF DESCRIPTION OF THE DRAWINGS

FIGS. 2-8 illustrate various use cases of hearing prostheses systems according to embodiments of the present disclosure.

DETAILED DESCRIPTION

The following detailed description describes various features, functions, and attributes with reference to the accompanying figures. In the figures, similar symbols typically identify similar components, unless context dictates otherwise. The illustrative embodiments described herein are not meant to be limiting. Certain features, functions, and attributes disclosed herein can be arranged and combined in a variety of different configurations, all of which are contemplated in the present disclosure. For illustration purposes, some features and functions are described with respect to medical devices, such as hearing prostheses. However, the features and functions disclosed herein may also be applicable to other types of devices, including other types of medical and non-medical devices.

Figure 1:
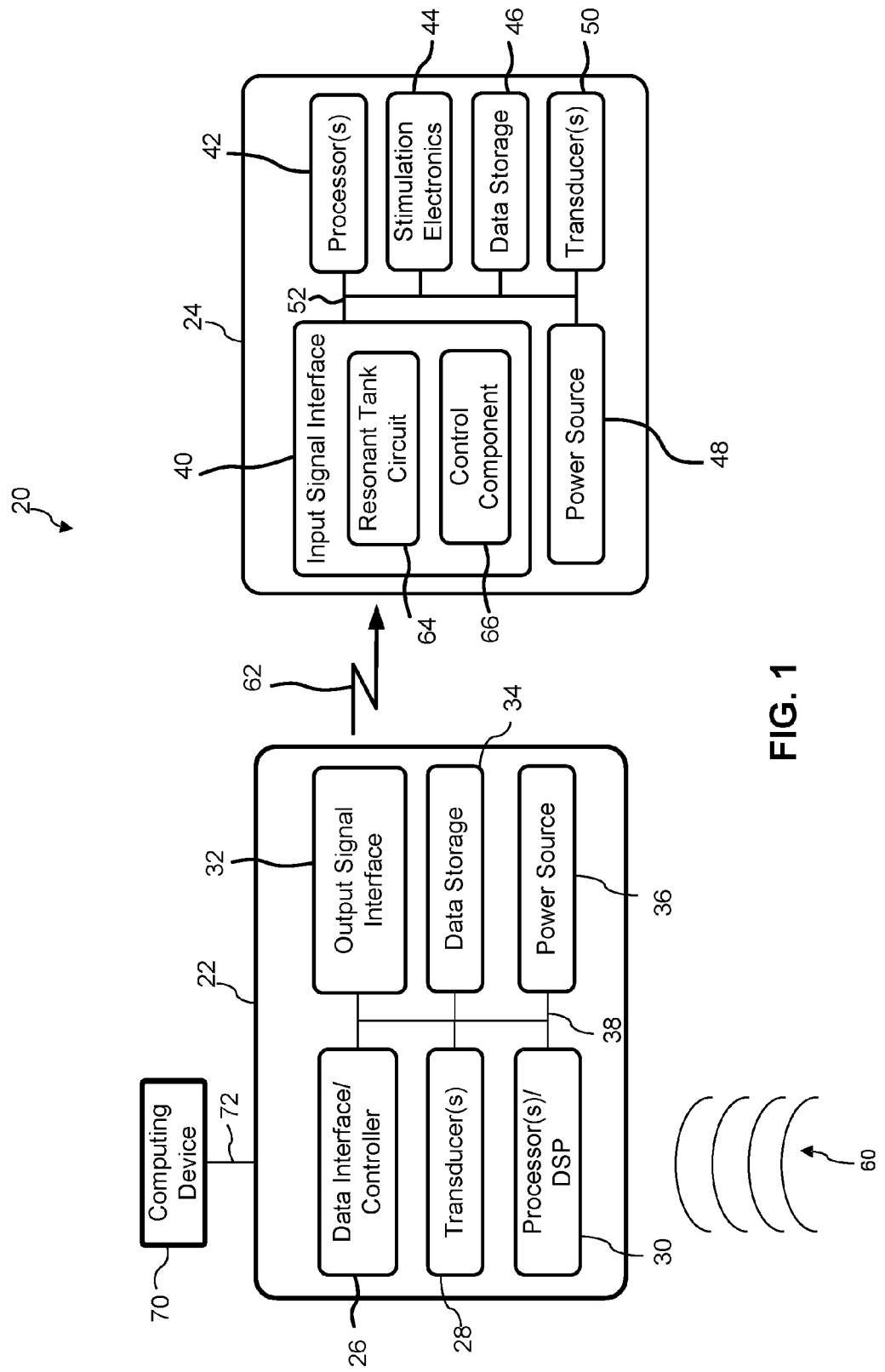
FIG. 1 illustrates a block diagram of a hearing prosthesis system according to an embodiment of the present disclosure.

Referring now to FIG. 1, an example electronic system 20 includes a first element or device 22 and a second element or device 24. The system 20 may include a hearing prosthesis, such as a cochlear implant, a bone conduction device, a direct acoustic cochlear stimulation device, an auditory brainstem implant, a bimodal hearing prosthesis, a middle ear stimulating device, or any other type of hearing prosthesis configured to assist a prosthesis recipient to perceive sound.

In this context, the first element 22 is configured to be generally external to a recipient and communicate with the second element 24, which is configured to be implanted in the recipient. Generally, an implantable element or device can be hermetically sealed and otherwise adapted to be at least partially implanted in a person.

In FIG. 1, the first element 22 includes a data interface 26 (such as a universal serial bus (USB) controller), one or more transducers 28, one or more processors 30 (such as digital signal processors (DSPs)), an output signal interface or communication electronics 32 (such as an electromagnetic radio frequency (RF) transceiver), data storage 34, and a power source 36 (such as a rechargeable battery), all of which may be coupled directly or indirectly via a wired conductor or wireless link 38. In the example of FIG. 1, the second element 24 includes an input signal interface or communication electronics 40 (such as an RF receiver), one or more processors 42, stimulation electronics 44, data storage 46, a power source 48 (such as a rechargeable battery), and one or more transducers 50, all of which are illustrated as being coupled directly or indirectly via a wired or wireless link 52.

Generally, the transducer(s) 28, 50 of the first and second elements 22, 24, respectively, are configured to receive external acoustic signals or audible sounds 60. Although, in practice, the transducers 28, 50 may not be configured to receive sounds 60 for further processing simultaneously. The transducer 28, 50 may include combinations of one or more omnidirectional or directional microphones configured to receive background sounds and/or to focus on sounds from a specific direction, such as generally in front of the prosthesis recipient. Alternatively or in addition, the transducers 28, 50 may include telecoils or other sound transducing components that receive sound and convert the received sound into electronic signals. Further, the system 20 may be configured to receive sound information from other sound input sources, such as electronic sound information received through the data interface 26 and/or through the input signal interface 40.

In one example, the processor 30 of the first element 22 is configured to process, amplify, encode, or otherwise convert the audible sounds 60 (or other electronic sound information) into encoded electronic signals that include audio data representing sound information, and to apply the encoded electronic signals to the output signal interface 32. In another example, the processor 42 of the second element 24 is also configured to process, amplify, encode, or otherwise convert the audible sounds 60 (or other electronic sound information) into encoded electronic signals that include audio data representing the sound information, and to apply the encoded electronic signals to the stimulation electronics 44. Generally, the processors 30, 42 are configured to convert the audible sounds or other electronic sound information into the encoded electronic signals in accordance with configuration settings or data for a prosthesis recipient. The configuration settings allow a hearing prosthesis to be configured for or fitted to a particular recipient. These configuration settings can be stored in the data storage 34, 46, for example.

The output signal interface 32 of the first element 22 is configured to transmit encoded electronic signals as electronic output signals 62 to the input signal interface 40 of the second element 24. As discussed above, the encoded electronic signals may include audio data representing sound information. The encoded electronic signals may also include power signals either with the audio data or without the audio data. Illustratively, the interfaces 32, 40 include magnetically coupled coils that establish an RF link between the elements 22, 24. Accordingly, the output signal interface 32 can transmit the output signals 62 encoded in a varying or alternating magnetic field over the RF link between the elements 22, 24.

Further, the processors 30, 42 are configured to transmit signals between the first and second elements in accordance with a communication protocol, the details of which may be stored in the data storage 34, 46, for example. The communication protocol defines how the stimulation data is transmitted from the first element 22 to the second element 24. Illustratively, the communication protocol may be an RF protocol that is applied after the stimulation data is generated to define how the stimulation data will be encoded in a structured signal frame format of the output signals 62. In addition to the stimulation data, the communication protocol defines how power signals are supplied over the structured signal frame format to provide a power flow to the second element 24.

Illustratively, the structured signal format includes output signal data frames for stimulation data and additional output signal power frames. In one example, the output signal power frames include pseudo-data to fill in partially a dead time associated with the signal, which facilitates a more continuous power flow to the second element when the encoded electronic signals include data and power. However, in other examples, additional output signal power frames are not necessary to transmit sufficient power along with stimulation data to the second element, because there may be enough "one" data cells of the stimulation data to provide power and/or a carrier wave of the output signals 62 may provide sufficient power. When the first element 22 transmits only power to the second element 24, the structured signal format may include only output signal power frames that are configured to provide a suitable amount of power to the second element 24 (e.g., for charging the power supply 48 and/or for providing operating power to the various components of the second element).

Once the processor 30 encodes the stimulation data and/or power signals using the communication protocol, the processor 30 may then provide the encoded stimulation data and/or power signals to the output signal interface 32, which in one example includes an RF modulator. The RF modulator is configured to modulate the encoded stimulation data and/or power signals with a carrier signal, e.g., a 5 MHz carrier signal, and the modulated 5 MHz carrier signal is transmitted over the RF link from the output signal interface 32 to the input signal interface 40. In various examples, the modulations can include OOK or frequency-shift keying (FSK) modulations based on RF frequencies between about 100 kHz and 50 MHz.

The second element 24 receives the output signals 62 via the input signal interface 40. In one example, the input signal interface 40 is an RF receiver system or circuit that includes a receiving coil and associated circuitry for receiving RF signals. In the example of FIG. 1, the input signal interface 40 also includes a resonant tank circuit or components 64 and control circuitry component 66.

In the context of transmitting the output signals 62 between the first element 22 and the second element 24, the system 20 is configured for multiple applications or modes. Illustratively, a first mode can be for applying stimulation data and operating power to the stimulation electronics 44 and a second mode can be for providing power signals to charge the power source 48. In this example, the first mode is a lower power use application than the second mode. The different power use levels of the first and second modes also correspond to different load conditions for the first and second modes. In order to improve the power efficiency of the first and second modes, the input signal interface 40 includes dual power supplies that are configured with first and second rectifier circuits. As will be described in more detail hereinafter, the first rectifier circuit is coupled to a receiving coil of the interface 40 over a parallel resonant tank and the second rectifier circuit is coupled to the receiving coil over a series resonant tank. The parallel resonant tank and the series resonant tank make use of the same inductive and capacitive components, e.g., the same LC circuit.

The processor 42 is configured to decode the received output signals 62 and extract the encoded electronic signals. As discussed above, the processor 42 is also configured generate encoded electronic signals directly from the sounds 60 received by the transducer 50. The second element 24 is configured to apply the encoded electronic signals to the stimulation electronics 44. The stimulation electronics 44 use the encoded electronic signals to generate an output that allows a recipient to perceive the encoded electronic signals as sound. In the present example, the stimulation electronics 44 include a transducer or actuator that provides auditory stimulation to the recipient through one or more of electrical nerve stimulation, audible sound production, or mechanical vibration of the cochlea, for instance.

The first and second components 22, 24 are also configured for backlink communications exchanged between the signal interfaces 32, 40. Such backlink communications can be used to control the electrical signals provided to the second component 24, and to control switching between different modes in the second component 24.

Referring back to the power sources 36, 48, each power source provides power to various components of the first and second elements 22, 24, respectively. In another variation of the system 20 of FIG. 1, one of the power sources may be omitted, for example, the system may include only the power source 36 or the power source 48, which is used to provide power to other components. The power sources 36, 48 can be any suitable power source, such as one or more non-rechargeable or rechargeable batteries. In one example, one or more of the power sources 36, 48 are batteries that can be recharged wirelessly, such as through inductive charging. Generally, a wirelessly rechargeable battery facilitates complete subcutaneous implantation of a device to provide a fully or at least partially implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined or otherwise, associated with use of the prosthesis.

Further, the data storage 34, 46 may be any suitable volatile and/or non-volatile storage components. The data storage 34, 46 may store computer-readable program instructions and perhaps additional data. In some embodiments, the data storage 34, 46 stores data and instructions used to perform at least part of the processes disclosed herein and/or at least part of the functionality of the systems described herein. Although the data storage 34, 46 in FIG. 1 are illustrated as separate blocks, in some embodiments, the data storage can be incorporated, for example, into the processor(s) 30, 42, respectively.

The system 20 illustrated in FIG. 1 further includes a computing device 70 that is configured to be communicatively coupled to the hearing prosthesis 22 via a connection or link 72. The link 72 may be any suitable wired connection, such as an Ethernet cable, a Universal Serial Bus connection, a twisted pair wire, a coaxial cable, a fiber-optic link, or a similar physical connection, or any suitable wireless connection, such as BLUETOOTH, WI-FI, WiMAX, inductive or electromagnetic coupling or link, and the like.

In general, the computing device 70 and the link 72 are used to operate the hearing prosthesis in various ways. In one example, the computing device and the link are used to adjust various parameters of the hearing prosthesis. The computing device and the link can also be used to load a recipient's configuration settings on the hearing prosthesis such as via the data interface 26. In another example, the computing device and the link are used to upload other program instructions and firmware upgrades to the hearing prosthesis. In yet other examples, the computing device and the link are used to deliver data (e.g., sound information) and/or power to the hearing prosthesis to control or adjust the components thereof and/or to charge a power supply. Still further, various other ways of operating the prosthesis can be implemented by utilizing the computing device and the link.

The computing device 70 can further include various additional components, such as a processor, a storage device, and a power source. Further, the computing device can include user interface or input/output devices, such as buttons, dials, a touch screen with a graphic user interface, and the like, that can be used to turn the prosthesis on and off, adjust the volume, adjust or fine tune the configuration data or parameters, etc. Thus, the computing device can be utilized by the recipient or a third party, such as a guardian of a minor recipient or a health care professional, to control or adjust the hearing prosthesis.

Various modifications can be made to the system 20 illustrated in FIG. 1. For example, a user interface or input/output devices can be incorporated into the first element 22 and/or the second element 24. Generally, the system 20 may include additional or fewer components arranged in any suitable manner. In some examples, the system 20 may include other components to process external audio signals, such as components that measure vibrations in the skull caused by audio signals and/or components that measure electrical outputs of portions of a person's hearing system in response to audio signals.

Figure 2:
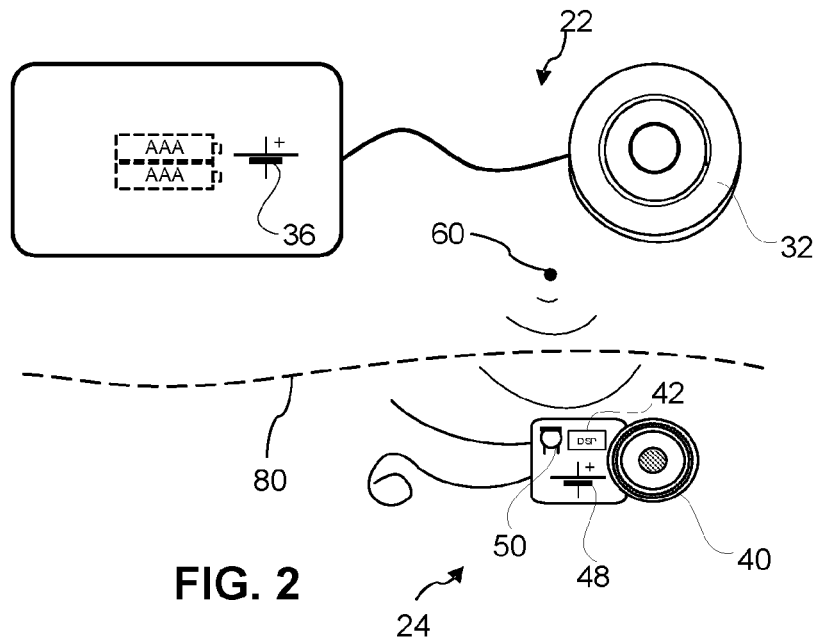

FIGS. 2-8 illustrate use cases of different configurations of the system of FIG. 1. Referring to FIG. 2, the first element 22 includes a power source 36, and an output signal interface 32 configured as a headpiece coil. In this example, the second element 24 includes a signal interface 40 configured as an implant coil, a processor 42, a power source 48, and transducer or microphone 50. In this use case, the power source 48 is in a state of low charge, and the second element 24 receives power from the first element 22 to charge the power source 48 and to provide operating power for other components of the second element, and the microphone 50 receives audible sounds 60 transcutaneously through skin 80 of a recipient of the hearing prosthesis.

Figure 3:
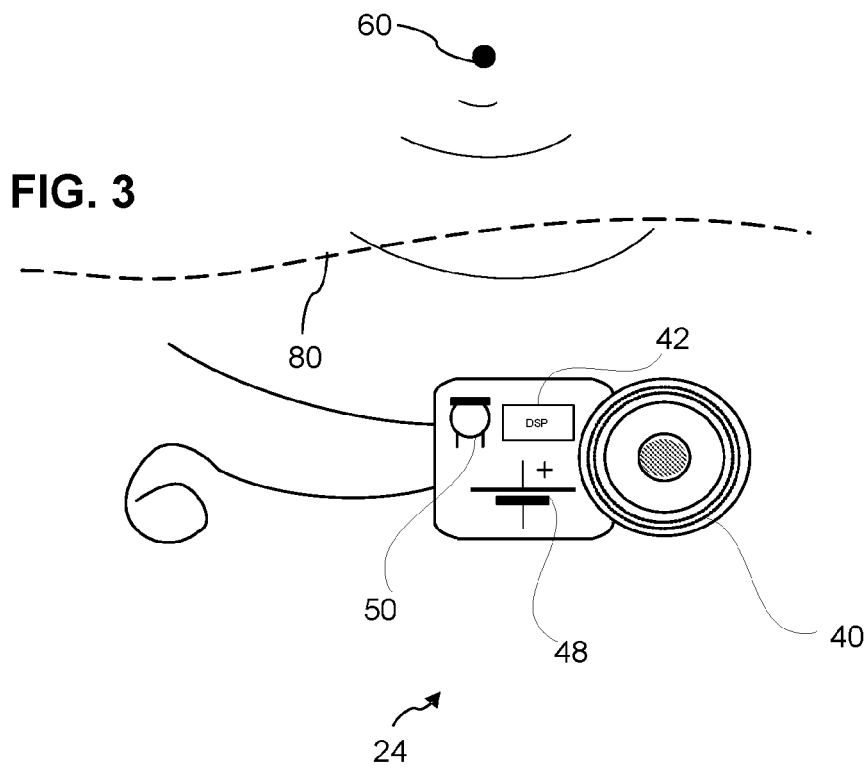

In FIG. 3, the second element 24 is similar to the second element of FIG. 2. In this use case, the second element 24 is powered by the power source 48, and receives audible sounds 60 transcutaneously through the skin 80 of the recipient.

In FIG. 4, the first element 22 is configured as a behind-the-ear component, and includes a transducer or microphone 28, a processor 30, a power source 36, and an output signal interface 32 configured as a headpiece coil. In this example, the second element 24 includes a signal interface 40 configured as an implant coil, a processor 42, a power source 48, and transducer or microphone 50. In this use case, the power source 48 of the second element 24 is reaching or has reached the end of its operative life (e.g., due to having been through a large number of charge/discharge cycles), and the second element 24 receives power from the first element 22 to operate the components of the second element. In this use case, the microphone 28 receives audible sounds 60, and the first element 22 processes the audible sounds and provides encoded electronic signals to the second element 24. Although, the microphone 50 may also receive audible sounds, and the processor 42 may convert the audible sounds into stimulation signals for application to the recipient.

In FIG. 5, the first element 22 is configured as a headpiece button device, and includes a transducer or microphone 28, a processor 30, a power source 36, and an output signal interface 32 configured as a headpiece coil. In this example, the second element 24 includes a signal interface 40 configured as an implant coil, a processor 42, a power source 48, and transducer or microphone 50. This use case is similar to FIG. 4, except a headpiece button device is utilized rather than the BTE device. The power source 48 of the second element 24 is reaching or has reached the end of its operative life, and the second element 24 receives power from the first element 22 to operate the components of the second element. In this use case, the microphone 28 receives audible sounds 60, and the first element 22 processes the audible sounds and provides encoded electronic signals to the second element 24. Although, the microphone 50 may also receive audible sounds, and the processor 42 may convert the audible sounds into stimulation signals for application to the recipient.

In FIG. 6, the first element 22 includes a transducer or microphone 28, a processor 30, a power source 36, and an output signal interface 32 configured as a headpiece coil. In this example, the second element 24 includes a signal interface 40 configured as an implant coil, and a power source 48. In this use case, the power source 48 of the second element 24 is in a state of low charge, and the second element 24 receives power from the first element 22 to charge the power source 48 and to provide operating power for other components of the second element. In this use case, the microphone 28 receives audible sounds 60, and the first element 22 processes the audible sounds and provides encoded electronic signals to the second element 24.

In FIG. 7, the first element 22 is configured as a headpiece button device, and includes a transducer or microphone 28, a processor 30, a power source 36, and an output signal interface 32 configured as an external coil. In this example, the second element 24 includes a signal interface 40 configured as an implant coil, and a power source 48. In this use case, the power source 48 of the second element 24 has sufficient charge to provide power to the components of the second element. In this use case, the microphone 28 receives audible sounds 60, and the first element 22 processes the audible sounds and provides encoded electronic signals to the second element 24.

Figure 8:
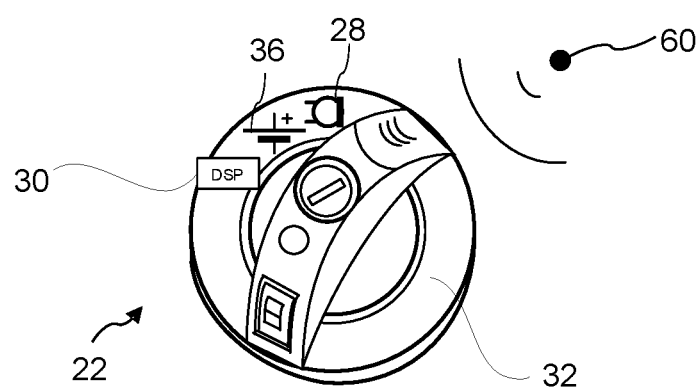
Figure 8:
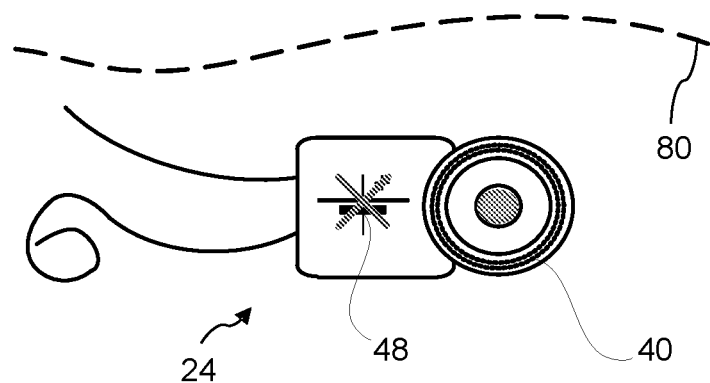

In FIG. 8, the first element 22 is configured as a headpiece button device, and includes a transducer or microphone 28, a processor 30, a power source 36, and an output signal interface 32 configured as an external coil. In this example, the second element 24 includes a signal interface 40 configured as an implant coil, and a power source 48. In this use case, the power source 48 of the second element 24 has sufficient charge to provide power to the components of the second element. In this use case, the power source 48 of the second element 24 is reaching or has reached the end of its operative life, and the second element 24 receives power from the first element 22 to operate the components of the second element. In this use case, the microphone 28 receives audible sounds 60, and the first element 22 processes the audible sounds and provides encoded electronic signals to the second element 24.

Figure 9:
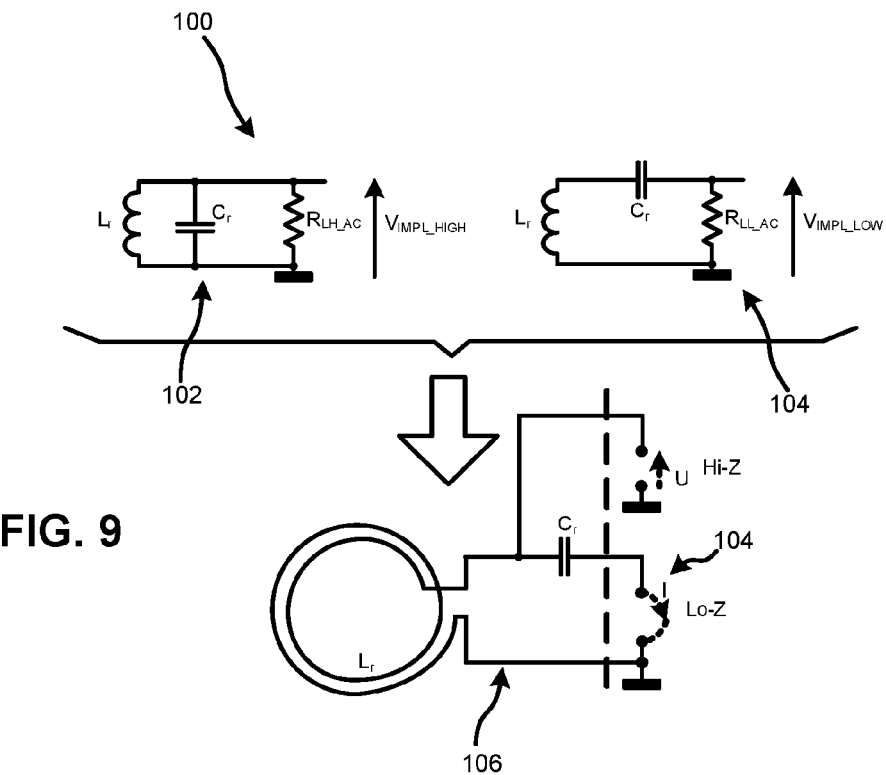
FIGS. 9-13 illustrate example power supply circuits according to embodiments of the present disclosure.

Referring now to FIG. 9, an LC resonant tank 100 is shown. In this example, $L_r$ represents an inductance of a coil in the second element 24, and Cr represents a tuning capacitor in the second element 24. More particularly, FIG. 9 provides an example of the input signal interface 40 of FIG. 1. FIG. 9 illustrates a parallel resonant tank circuit 102 and a series resonant tank circuit 104, and a configuration of the tank circuits 102, 104 into a combined resonant tank circuit 106. In practice, a rechargeable battery is connected to the 'Lo-Z' port, and stimulation electronics are connected to the 'Hi-Z' port. A resonance frequency of the parallel or series tank is given by Equation 1:

$$f_0 = \frac{\omega_0}{2\pi} = \frac{1}{2\pi\sqrt{LC}}. \quad (1)$$

The example of FIG. 9 integrates a dual power supply configuration using a low component count. In this example, the hearing prosthesis is configured to extract power (and data) for a first mode of operation from the parallel resonant tank circuit 102, such as by using a half-wave rectifier. Further, the hearing prosthesis is configured to charge a power source or battery through the series resonant tank circuit 104, such as by using a voltage doubler.

Figure 10:
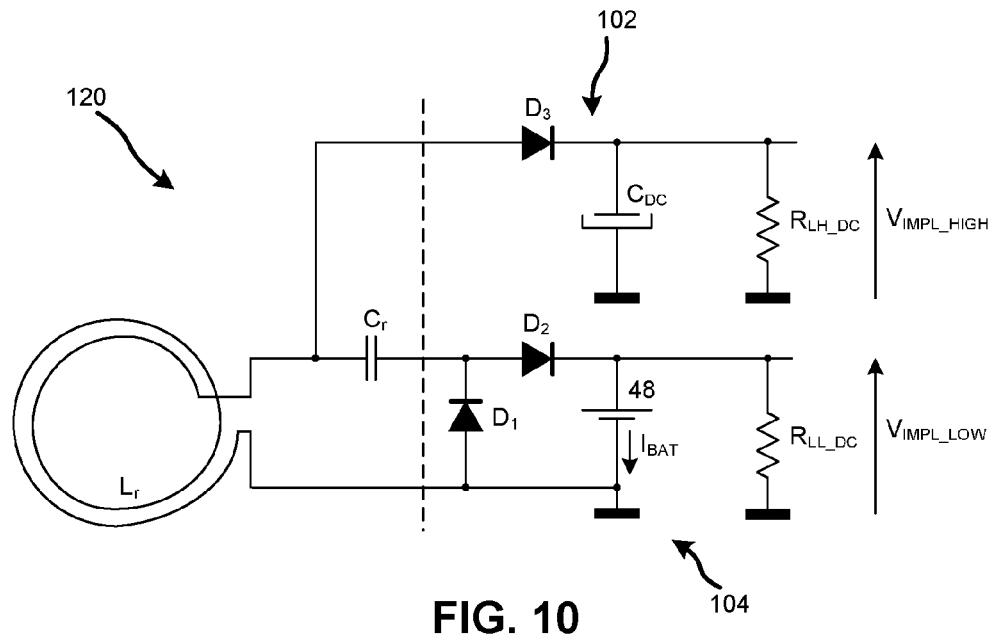

FIG. 10 illustrates another LC resonant tank 120 that includes a voltage doubler, which in this example includes diodes $D_1$ and $D_2$ coupled to a power supply 48. The resonant tank 120 also includes a half-wave rectifier, which in this example includes a diode $D_3$ in series with a load represented by, or coupled across $R_{LH\_DC}$. Generally, the resistance $R_{LH\_DC}$ represents a load that has relatively low current demands (e.g., stimulator electronics). The resistance $R_{LL\_DC}$ represents a load that has relatively high current demands (e.g., a voltage step-up conversion component and/or the power source that is to be recharged).

Figure 11:
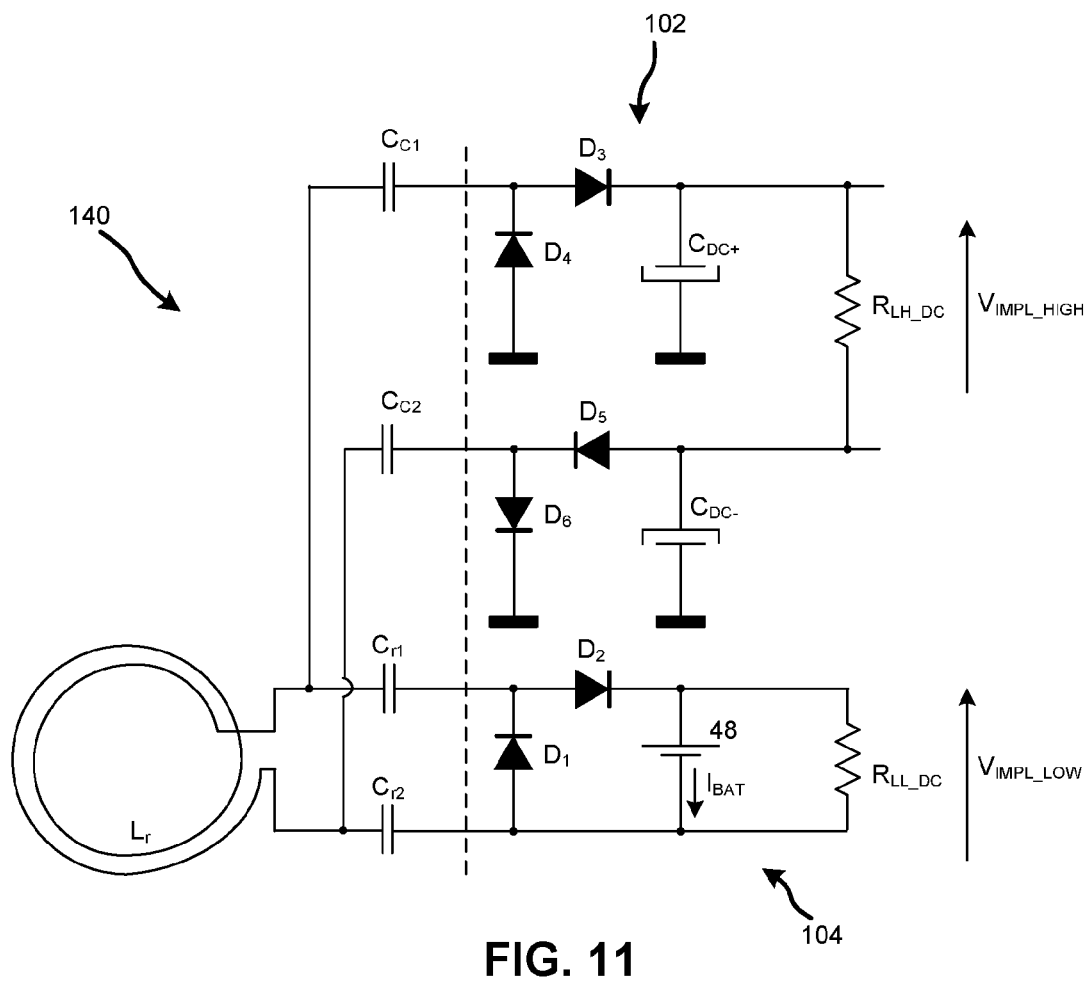

FIG. 11 illustrates an LC resonant tank 140 that is similar to the tank 120 of FIG. 10, but includes additional grounding components to provide a more symmetrical circuit that helps to provide more balanced inputs. The tank 140 includes decoupling capacitors $C_{r1}$, $C_{r2}$, $C_{c1}$, and $C_{c2}$.

Figure 12:
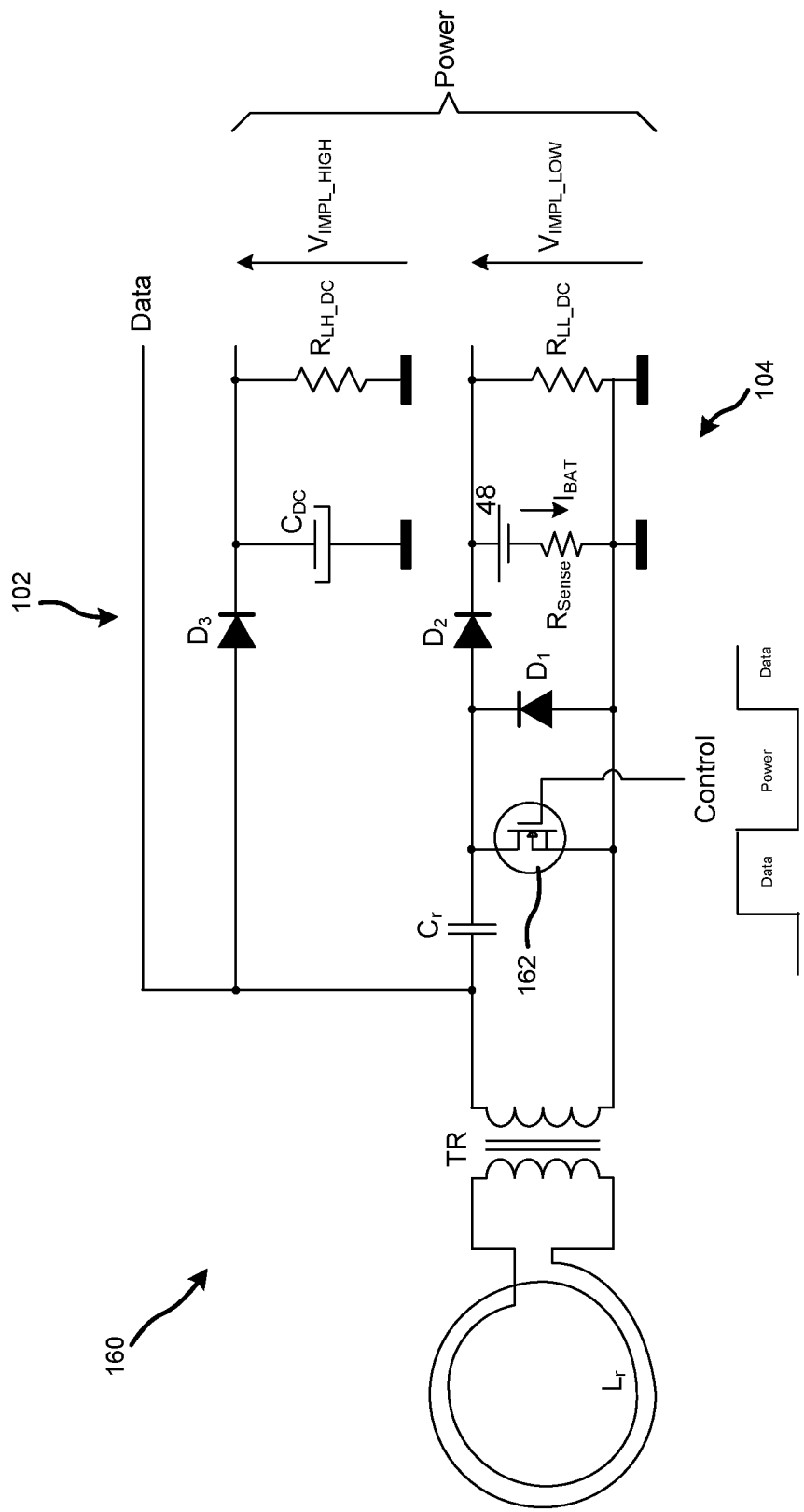

FIG. 12 illustrates an LC resonant tank 160 that includes an additional transformer TR that is coupled to the coil $L_r$ and configured to provide DC insulation and implant voltage step-up. In this example, the transformer TR is useful when the coil Lr includes a low number of coil wraps or turns (e.g., two turns). The transformer TR is also useful to improve electrical insulation between the coil Lr and other components (e.g., stimulation electronics 44). Further, improving electrical insulation also helps to prevent the flow of tissue current leakages and helps to prevent the coil providing a return path electrode for multi-polar stimulation.

The tank 160 also includes a switching or control component 162, such as a MOSFET switch. The control component 162 is coupled to a control signal that is provided by the processor 42, for instance. In one example, the processor 42 monitors operating conditions, such as the charge state or battery life of the power source 48, the operative life of the power source 48, the presence of stimulation data in signals received by the coil $L_r$, and/or the presence of the power source 36 of the first element 22 to provide power to the second element 24.

In one example, the processor 42 monitors the charge state of the power source 48 by measuring current through and/or voltage over the power source 48. In this example, the processor 42 measures power source current by sensing the current through a resistor $R_{Sense}$ coupled in series with the power source 48. Generally, the processor 42 is configured to correlate the measured current (or a measured voltage over the power source 48 or resistor $R_{Sense}$) to a remaining charge level of the power source. When the processor 42 detects that the battery life is below a predetermined threshold (e.g., the charge state of the power source 48 is low), the processor 42 controls the component 162 to form an open circuit and allow power signals received by the coil $L_r$ to flow and charge the power source 48.

When the processor 42 detects that the battery life is above a predetermined threshold (e.g., the charge state of the power source 48 indicates an adequate charge), the diode $D_2$ represents a high impedance load, and the processor 42 controls the component 162 to be closed and to short the tuning capacitor $C_r$ to ground. This arrangement avoids charging the power source 42, and instead, signals received by the coil $L_r$ are provided to the parallel tank circuit 102, and may be used to provide data and/or operating power directly to components of the second element 24. This arrangement also helps to prevent the parallel tank from suffering from a lower quality factor Q, which thus helps to improve the RF link power transfer efficiency.

In another example, the processor 42 monitors the operative life of the power source 42 by tracking charge/discharge cycles, and determining if the charge/discharge cycles are approaching an expected cycle limit associated with the end of the operative life of the power source 42. Alternatively or in conjunction, the processor monitors the operative life of the power source by determining that the charge state of the power source is not increasing as expected during or after a charge cycle. When the processor detects that the power source is approaching or has reached the end of its operative life, the power source is considered to represent an open current circuit. In this case, the processor controls the component 162 to short the tuning capacitor $C_r$ to ground, such that a low impedance state is obtained at the 'Lo-Z' port. Signals received by the coil $L_r$ are then provided to the parallel tank circuit 102, and may be used to provide data and/or operating power directly to components of the second element 24.

In this example, the component 162 is controlled to decouple the power source 48, which can also be useful, for instance, in the scenario when data and power signals are being received by the coil $L_r$ in different time slots. More particularly, in this scenario it is generally preferred that during a data time slot the power source 48 is not extracting power from the data signals.

In a further example, the processor 42 processes electrical signals received by the coil $L_r$ to determine if the electrical signals include stimulation data, which may be provided alone or with power signals. Responsive to determining that the electrical signals include stimulation data, the processor 42 is configured to control the component 162 to short the tuning capacitor $C_r$ to ground, and consequently to provide the stimulation data through the parallel tank circuit 102. As will be described in more detail hereinafter, the stimulation data is provided to a processor that is configured to extract the stimulation data and provide the stimulation data to stimulation electronics for application to a recipient of the hearing prosthesis.

In another example, the processor 42 controls the component 162 to alternate between open and closed states, for instance, to transfer power to the battery in bursts. More particularly, the component 162 is open during a power burst and is closed during a modulated OOK data transfer. In this example, data and power signals may be received by the coil $L_r$ in different time slots, and the processor is configured to control the component so that during a data time slot the power source 48 is not extracting power from the data signals.

The present disclosure also contemplates including the control component 162 (e.g., a MOSFET or other switching component coupled between the tuning capacitor $C_r$ and ground) in the tank circuits of FIGS. 9, 10, and 11.

Figure 13:
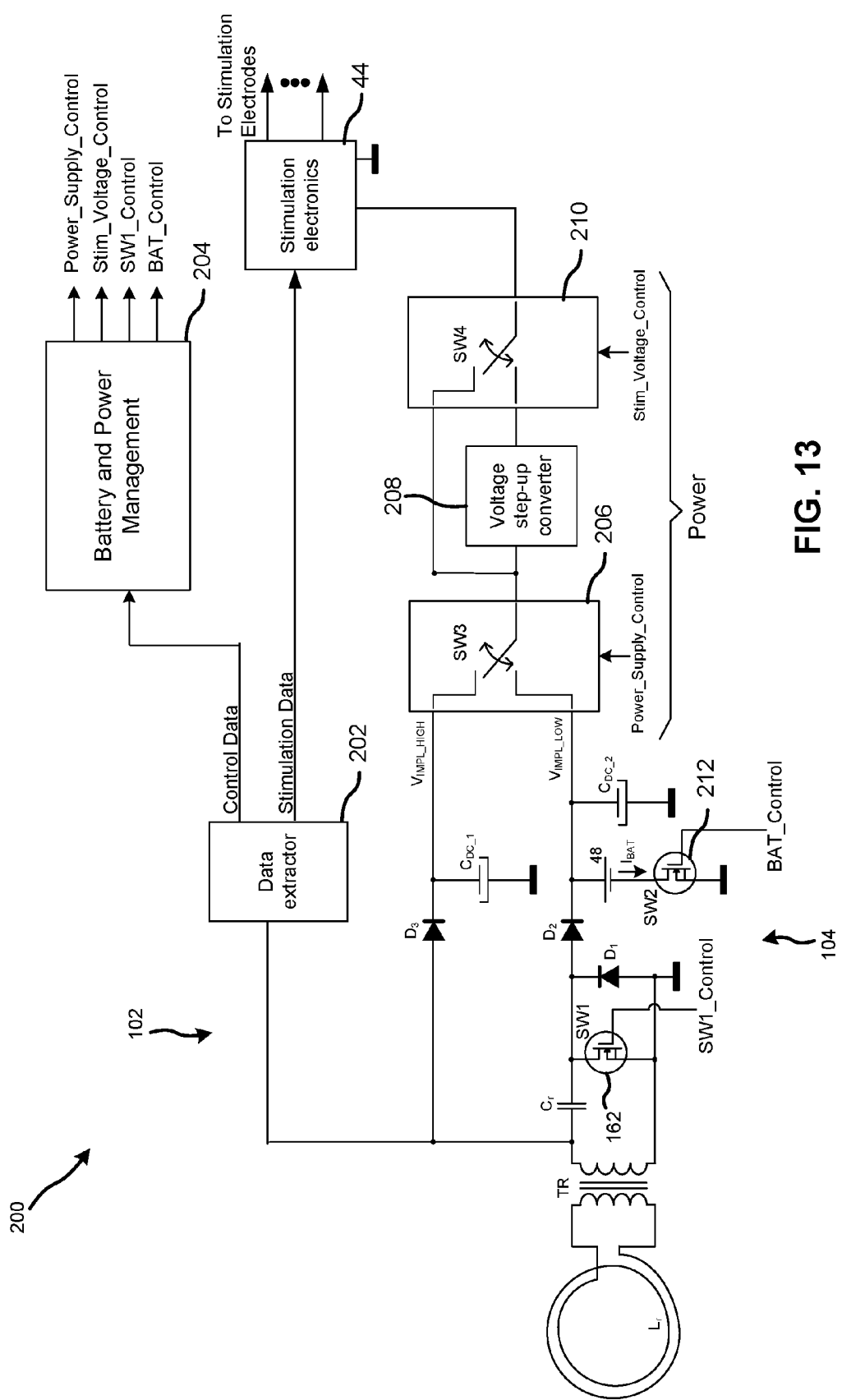

FIG. 13 illustrates another LC resonant tank 200 that illustrates stimulation electronics 44, a data extractor component or processor 202, a battery and power management component or processor 204, and other components coupled to components of the tank 160 of FIG. 12. More particularly, in FIG. 13, the data extractor 202 is coupled to the parallel resonant tank circuit 102, and is configured to extract control data and stimulation data from signals received by the coil $L_r$. The extracted control data are provided to the management component 204, which is configured to generate additional control signals based on the extracted control data. As shown, the additional control signals include a power supply control signal (Power_Supply_Control), a stimulation voltage control signal (Stim_Voltage_Control), a switch control signal (SW1_Control), and a battery control signal (BAT_Control). In addition, the extracted stimulation data is provided to the stimulation electronics 44, which are configured to use the stimulation data to apply output signals to the recipient's hearing system through stimulation electrodes, for instance.

The stimulation electronics in FIG. 13 are configured to receive power from either or both of the parallel resonant tank circuit 102 and the series resonant tank circuit 104. In FIG. 13, the stimulation electronics 44 are coupled to the tank circuits 102, 104 through a control component 206 (e.g., a MOSFET switch SW3), which is coupled to a voltage step-up converter 208, which in turn is coupled to a control component 210 (e.g., a MOSFET switch SW4), and to the stimulation electronics. In FIG. 13, the control component 162 is also identified as a switch SW1, and an additional control component 212 (e.g., a MOSFET switch SW2) is coupled between the power source 48 and ground.

In the present example, the management component 204 is also configured to monitor the charge state or battery life of the power source 48 and the operative life of the power source 48, for instance. The management component 204 may also be configured to monitor other operating conditions, as disclosed herein, for example. Based on the monitored operating conditions, the management component 204 generates appropriate controls signals to operate the second element 24. More particularly, the management component 204 generates the power supply control signal that controls the control component 206, the stimulation voltage control signal that controls the control component 210, the switch control signal that controls the control component 162, and the battery control signal that controls the control component 212.

In one example configuration, the power supply control signal (Power_Supply_Control) controls the control component 206 to selectively provide power to the stimulation electronics 44 from the power source 48 (e.g., $V_{IMPL\_LOW}$) or from the parallel tank circuit 102 ($V_{IMPL\_HIGH}$). The stimulation voltage control signal (Stim_Voltage_Control) controls the control component 208 to increase the voltage provided to the stimulation electronics 44 using the voltage step-up converter 208 or to bypass the step-up converter, as needed to operate the stimulation electronics. The switch control signal (SW1_Control) controls the control component 162 to switch between use of the parallel tank circuit 102 and the series tank circuit 104, for instance, to deliver stimulation data through the parallel tank circuit or to deliver power to charge the power source 48 through the series tank circuit. The battery control signal (BAT_Control) controls the control component 212 to disconnect the power source 48 when the power source is approaching or has reached the end of its operative life.

The embodiments of FIGS. 9-13 may be used with the hearing prosthesis system of FIG. 1 in the use cases of FIGS. 2-8 to provide flexibility and expand the functionality of hearing prostheses in general. Potential advantages and benefits include (a) being able to deactivate a battery of an implanted component when the battery is nearing the end of its operative life (e.g., due to having been through a large number of charge/discharge cycles) and thus extending operation of the hearing prosthesis system; (b) facilitating control of how often battery power is relied upon as a way of extending the battery life; and (c) charging a battery of an implanted component while providing flexibility regarding receiving audible sounds from an external and/or an internal hearing prosthesis component.

The embodiments disclosed herein also provide efficient transcutaneous power transfer in different operating modes (e.g., data transfer and battery recharging modes). Generally, the series tank disclosed herein provides a current controlled recharge of a battery, and the parallel tank provides a voltage controlled supply to provide power to the second element when the battery is not being used or has a low power level. The RF link configuration can be useful for slowly charging the battery from a standard power supply (e.g., two Zn-air hearing aid batteries) during a data transfer mode, as well.

Another potential benefit is the use of the same discrete inductive and capacitive components for both the series and parallel resonant tanks. In addition, the processor 42 may effectively provide a voltage controlled power supply and a current controlled battery recharge by controlling a switching components, as discussed above in relation to FIG. 12.

Figure 14:
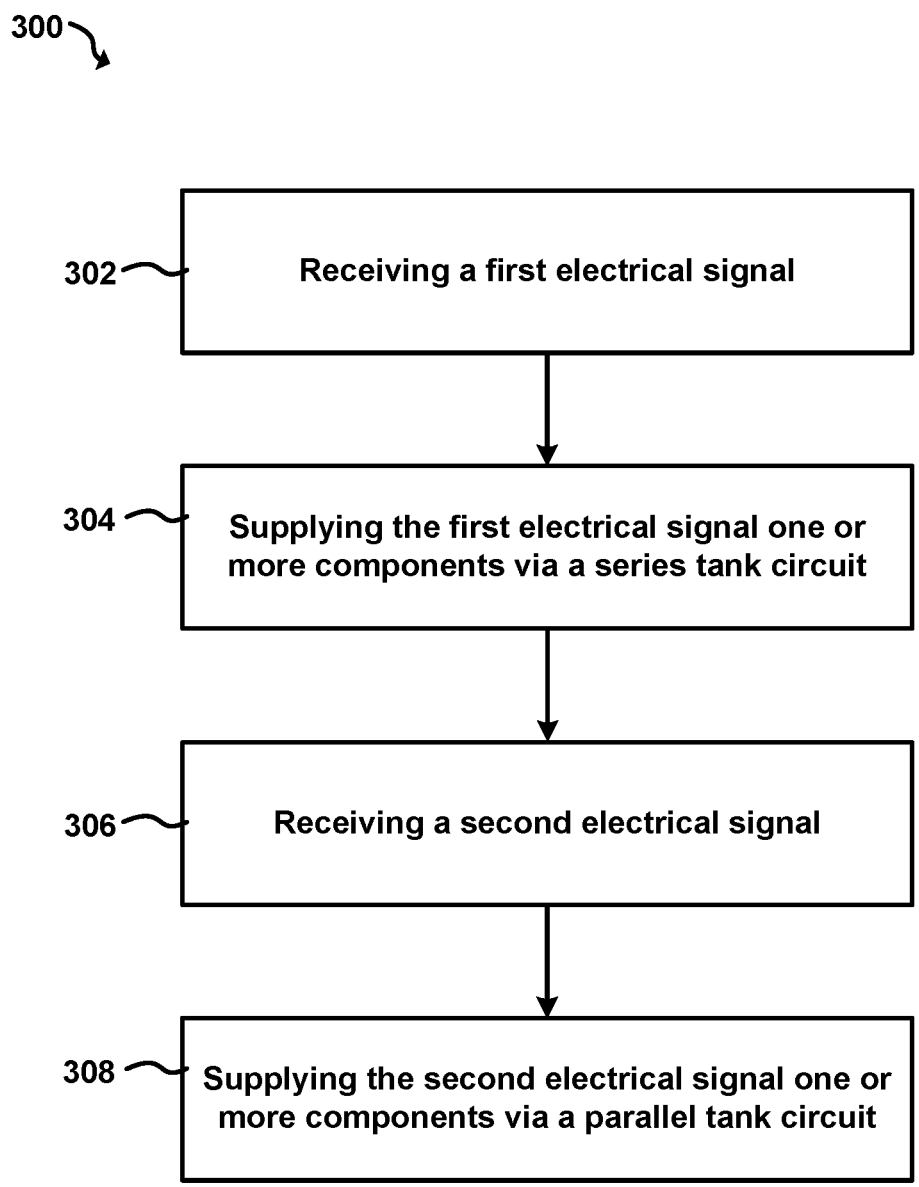
FIG. 14 is an example method according to an embodiment of the present disclosure.

Referring now to FIG. 14, an example method 300 is illustrated, which can be implemented by the system of FIG. 1 utilizing the tank circuits of FIGS. 9-13, for instance. Generally, the method 300 may include one or more operations, functions, or actions as illustrated by one or more of blocks 302-308. Although the blocks 302-308 are illustrated in a particular order, these blocks may also be performed in a different order than illustrated, and some blocks may even be omitted and other blocks may be added according to certain implementations.

In addition, one or more of blocks 302-308 may represent a module, a segment, or a portion of program code, which includes one or more instructions executable by a processor for implementing specific logical functions or steps in the process. The program code may be stored on any type of computer readable medium or storage device including a disk or hard drive, for example. The computer readable medium may include non-transitory computer readable medium, such as computer-readable media that stores data for short periods of time like register memory, processor cache, and Random Access Memory (RAM). The computer readable medium may also include non-transitory media, such as secondary or persistent long term storage, like read only memory (ROM), optical or magnetic disks, compact-disc read only memory (CD-ROM), etc. The computer readable media may also include any other volatile or non-volatile storage systems. The computer readable medium may be considered a computer readable storage medium, for example, or a tangible storage device. In addition, one or more of the blocks 302-308 may represent circuitry, e.g., the tanks circuits described herein, configured to perform the specific logical functions of the method 300.

In FIG. 14, at block 302, receiver circuitry of a device, such as a coil and/or electrical components coupled thereto, receives a first electrical signal over a wireless link. In this example, the first electrical signal is configured to charge a battery or power source of a device, such as a hearing prosthesis. At block 302, the receiver circuitry supplies or provides the first electrical signal to charge the battery or power source via a series tank circuit.

In one illustrative example, processes of the blocks 302, 304 are performed using the resonant tank 160 of FIG. 12. In this context, the coil $L_r$ receives the first electrical signal, which is a battery charging signal provided by the first element 22 of FIG. 1, for example. The tank 160 provides the first electrical signal to primary windings of a transformer TR. The first electrical signal is induced across the primary windings to second windings of the transformer. In the present example, the processor 42 controls the switching component 162 to operate in an open state. In this state of the tank 160, the first electrical signal is provided through the series tank (e.g., $L_r$, TR, $C_r$, $D_1$, and $D_2$) to charge the battery $BAT_1$.

In a variation of this example of the processes of the blocks 302, 304, data may be extracted from the first electrical signal provided via the series tank circuit. For instance, the processor 42 of the second component 24 is configured to count cycles of the first electrical signal that are above a fixed threshold current to extract data. This data may represent sound information that is applied to the stimulation electronics 44, for example.

Referring back to FIG. 14, at block 304, receiver circuitry of the device, such as the coil and/or electrical components coupled thereto, receives a second electrical signal over the wireless link. In this example, the second electrical signal is configured to provide data representing sound information and optionally operating power for other components of the device. As discussed herein, these other components include stimulation electronics of a hearing prosthesis. At block 306, the receiver circuitry supplies or provides the second electrical signal to the other components of the device via a parallel tank circuit. As discussed herein, the series tank circuit and the parallel tank circuit utilize the same inductance component(s) and the same capacitance component(s).

In one illustrative example, processes of the blocks 306, 308 are also performed using the resonant tank 160 of FIG. 12. In this context, the coil $L_r$ receives the second electrical signal, which includes encoded sound information and also power that can be used to operate stimulation electronics 44 of FIG. 1, for example. The tank 160 provides the second electrical signal to primary windings of a transformer TR. The second electrical signal is induced across the primary windings to second windings of the transformer. In the present example, the processor 42 controls the switching component 162 to operate in a closed state, and to short the capacitor $C_r$ to ground. In this state of the tank 160, the second electrical signal is provided through the parallel tank (e.g., $L_r$, TR, $C_r$, $D_3$, and $C_{DC}$) to actuate the stimulation electronics 44 in accordance with the second electrical signal. In one example, the processor 42 is configured to extract data from the second electrical signal by counting cycles of the second electrical signal that are above a fixed threshold voltage. Further, in this example, the parallel tank circuit and the series tank circuit share the same inductance component, $L_r$, and the same capacitance component, $C_r$.

While various aspects and embodiments have been disclosed herein, other aspects and embodiments will be apparent to those skilled in the art. The various aspects and embodiments disclosed herein are for purposes of illustration and are not intended to be limiting.

The invention claimed is:

1. A device comprising:
 a tank circuit comprising at least one inductive component and at least one capacitive component electrically connected to one another;
 medical device stimulation electronics connected in parallel with the at least one capacitive component such that the at least one inductive component and the at least one capacitive component form a parallel tank circuit relative to the medical device stimulation electronics;
 a rechargeable battery circuit connected in series with the at least one capacitive component such that the at least one inductive component and the at least one capacitive component form a series tank circuit relative to the rechargeable battery circuit; and
 circuitry comprising at least one switching component connected between the at least one capacitive component and ground, wherein the least one switching component is configured to be selectively closed to only provide one or more of power and data received at the at least one inductive component to the medical device stimulation electronics via the parallel tank circuit, and wherein the least one switching component is configured to be selectively opened to provide power received at the at least one inductive component to the rechargeable battery circuit via the series tank circuit.

2. The device of claim 1, wherein the medical device stimulation electronics include hearing prosthesis stimulation electronics.

3. The device of claim 2, further comprising a microphone electrically connected to the hearing prosthesis stimulation electronics and configured to receive sound signals, wherein the tank circuit, the circuitry, the rechargeable battery circuit, the hearing prosthesis stimulation electronics, and the microphone are hermetically sealed within a single operational unit.

4. The device of claim 1, wherein the medical device stimulation electronics comprise a first rectifier circuit connected to the parallel tank circuit, and wherein the rechargeable battery circuit comprises at least one rechargeable battery and a second rectifier circuit connected between the at least one rechargeable battery and the series tank circuit.

5. The device of claim 1, further comprising a controller coupled to the circuitry and configured to selectively open or close the at least one switching component.

6. The device of claim 5, wherein the rechargeable battery circuit comprises at least one rechargeable battery, and wherein the controller is configured to:
 detect when a life of the at least one rechargeable battery is below a predetermined threshold; and
 in response to detecting that the life of the at least one rechargeable battery is below the predetermined threshold, open the at least one switching component to allow power received via the at least one inductive component to flow to the rechargeable battery circuit.

7. The device of claim 5, wherein the controller is configured to:
 detect when a life of the at least one rechargeable battery is above a predetermined threshold; and
 in response to detecting that the life of the at least one rechargeable battery is above the predetermined threshold, close the at least one switching component to short the at least one capacitive component to ground and prevent the power received via the at least one inductive component from flowing to the rechargeable battery circuit.

8. The device of claim 5, wherein the rechargeable battery circuit comprises at least one rechargeable battery, and wherein the controller is configured to:
 monitor an operative life of the at least one rechargeable battery;
 determine that the rechargeable battery has reached the end of its operative life; and in response to determining that the at least one rechargeable battery has reached the end of its operative, close the at least one switching component to short the at least one capacitive component to ground and prevent the power received via the at least one inductive component from flowing to the rechargeable battery circuit.

9. The device of claim 8, wherein to monitor an operative life of the at least one rechargeable battery, the controller is configured to:
track a number of charge/discharge cycles of the at least one rechargeable battery; and
predetermine whether the number of charge/discharge cycles are near an expected cycle limit associated with the end of the operative life of the at least one rechargeable battery.

10. The device of claim 1, further comprising a transformer coupled between the at least one inductive component and the resonant tank circuit.

11. The device of claim 1, wherein the at least one switching component includes a transistor switch.

12. A method comprising:
receiving, by at least one inductive component of a medical device, a first electrical signal over a wireless link, wherein the at least one inductive component is part of a resonant tank circuit that also comprises at least one capacitive component, and wherein at least one switch is connected between the at least one capacitive component and ground, and
wherein the medical device comprises medical device stimulation electronics connected in parallel with the at least one capacitive component such that the at least one inductive component and the at least one capacitive component form a parallel tank circuit relative to the medical device stimulation electronics, and wherein the medical device comprises a rechargeable battery circuit connected in series with the at least one capacitive component such that the at least one inductive component and the at least one capacitive component form a series tank circuit relative to the rechargeable battery circuit;
selectively opening the at least one switch to supply the first electrical signal to the rechargeable battery of the device via the at least one inductive component and the at least one capacitive component connected to form the series tank circuit relative to the rechargeable battery;
receiving, by the at least one inductive component, a second electrical signal over the wireless link; and
selectively closing the at least one switch to supply the second electrical signal to only the medical device stimulation electronics of the device via the at least one inductive component and the at least one capacitive component connected to form the parallel tank circuit relative to the medical device stimulation electronics.

13. The method of claim 12, wherein the device is a hearing prosthesis, and wherein the medical device stimulation electronics include hearing prosthesis stimulation electronics.

14. The method of claim 13, wherein the device further includes a microphone electrically connected to the hearing prosthesis stimulation electronics and configured to receive sound signals.

15. The method of claim 14, further comprising:
receiving, by the microphone, audible sounds through skin of a recipient of the hearing prosthesis;
converting the audible sounds into stimulation signals; and
applying, using the hearing prosthesis stimulation electronics, the stimulation signals to the recipient.

16. The method of claim 12, further comprising:
detecting when a life of the rechargeable battery is below a predetermined threshold; and
opening the at least one switch only in response to detecting that the life of the rechargeable battery is below the predetermined threshold.

17. The method of claim 12, further comprising:
monitoring an operative life of the rechargeable battery;
determining that the rechargeable battery has reached the end of its operative life; and
in response to determining that the rechargeable battery has reached the end of its operative, closing the at least one switch to short the at least one capacitive component to ground.

18. An implantable medical device, comprising:
a resonant tank circuit comprising a capacitive component, an inductive component, a first output node, and a second output node, wherein at least one inductive component is connected to the capacitive component and is configured to receive signals from an external coil;
medical device stimulation electronics connected to the first output node of the resonant tank circuit;
a rechargeable battery circuit connected to the second output node of the resonant tank circuit; and
circuitry comprising at least one switch connected between the at least one capacitor and ground configured to be selectively closed to couple the capacitive component and the inductive component in parallel with one another to form a parallel tank circuit useable to provide one or more of power and data received at the inductive component to only the medical device stimulation electronics, and to be selectively opened to couple the capacitive component and the inductive component in series with one another to form a series tank circuit useable to provide power received at the inductive component to the rechargeable battery circuit.

19. The device of claim 18, wherein the medical device stimulation electronics comprise a first rectifier circuit connected to the first output node, and wherein the rechargeable battery circuit comprises at least one rechargeable battery and a second rectifier circuit connected between the at least one rechargeable battery and the second output node.

20. The device of claim 18, wherein the rechargeable battery circuit comprises at least one rechargeable battery, and wherein the circuitry comprises a controller configured to:
detect when a life of the at least one rechargeable battery is below a predetermined threshold; and
in response to detecting that the life of the at least one rechargeable battery is below the predetermined threshold, open the at least one switch to allow power received via the at least one inductive component to flow to the rechargeable battery circuit.

21. The device of claim 20, wherein the controller is configured to:
detect when a life of the at least one rechargeable battery is above a predetermined threshold; and
in response to detecting that the life of the at least one rechargeable battery is above the predetermined threshold, close the at least one switch to short the at least one capacitive component to ground and prevent the power received via the at least one inductive component from flowing to the rechargeable battery circuit.

22. The device of claim 18, wherein the rechargeable battery circuit comprises at least one rechargeable battery, and wherein the circuitry comprises a controller configured to:
  monitor an operative life of the at least one rechargeable battery;
  determine that the rechargeable battery has reached the end of its operative life; and
  in response to determining that the at least one rechargeable battery has reached the end of its operative, close the at least one switch to short the at least one capacitive component to ground and prevent the power received via the at least one inductive component from flowing to the rechargeable battery circuit.

23. The device of claim 18, further comprising a transformer coupled between the inductive component and the capacitive component.

\* \* \* \* \*